United States Patent [19]

Fuchs et al.

[11] Patent Number: 4,611,009
[45] Date of Patent: * Sep. 9, 1986

[54] COMBATING ARTHROPODS WITH 3-PHENOXYBENZYL 2,2-DIMETHYL-3-VINYLCYCLOPROPANE CARBOXYLATES

[75] Inventors: Rainer Fuchs, Wuppertal; Ingeborg Hammann, Cologne; Wilhelm Stendel, Wuppertal, all of Fed. Rep. of Germany

[73] Assignee: Bayer Aktiengesellschaft, Leverkusen, Fed. Rep. of Germany

[*] Notice: The portion of the term of this patent subsequent to Jun. 30, 1998 has been disclaimed.

[21] Appl. No.: 391,732

[22] Filed: Jun. 24, 1982

Related U.S. Application Data

[62] Division of Ser. No. 195,026, Oct. 8, 1980, abandoned, which is a division of Ser. No. 135,070, Mar. 28, 1980, which is a division of Ser. No. 916,163, Jul. 16, 1978, Pat. No. 4,276,306.

[30] Foreign Application Priority Data

Jul. 6, 1977 [DE] Fed. Rep. of Germany ....... 2730515

[51] Int. Cl.$^4$ .................... C07C 121/60; A01N 43/36
[52] U.S. Cl. ...................... 514/521; 558/407
[58] Field of Search .............. 560/8; 260/465 D; 424/274, 308

[56] References Cited

U.S. PATENT DOCUMENTS

| 3,666,789 | 5/1972 | Itaya | 560/124 |
| 3,835,176 | 9/1974 | Matsuo | 560/124 |
| 4,024,163 | 5/1977 | Elliott | 560/124 |
| 4,157,397 | 6/1979 | Engel | 560/124 |
| 4,157,447 | 6/1977 | Engel | 560/124 |
| 4,200,644 | 4/1980 | Engel | 424/274 |
| 4,358,409 | 11/1982 | Hoffmann | 560/124 |

Primary Examiner—Michael L. Shippen
Attorney, Agent, or Firm—Sprung Horn Kramer & Woods

[57] ABSTRACT

3-Phenoxybenzyl 2,2-dimethyl-3-vinyl-cyclopropane carboxylates of the formula

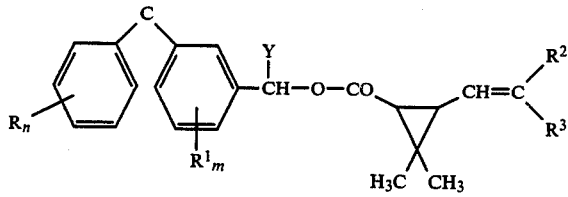

in which
R, $R^1$ and $R^2$ each independently is hydrogen or halogen,
$R^3$ is phenyl, phenylthio, or phenyl or phenylthio carrying at least one alkyl group or halogen atom,
Y is hydrogen or cyano,
n is 1, 2, 3, 4 or 5, and
m is 1, 2, 3 or 4,
which possess arthropodicidal properties.

7 Claims, No Drawings

COMBATING ARTHROPODS WITH 3-PHENOXYBENZYL 2,2-DIMETHYL-3-VINYLCYCLOPROPANE CARBOXYLATES

This application is a division of Application Ser. No. 195,026 filed Oct. 8, 1980, now abandoned, which is a division of Application Ser. No. 135,070 filed Mar. 28, 1980, now pending, which is a division of Application Ser. No. 916,163, filed July 16, 1978, now U.S. Pat. No. 4,276,306.

The present invention relates to and has for its objects the provision of particular new 3-phenoxybenzyl 2,2-dimethyl-3-vinylcyclopropane carboxylates which possess arthropodicidal properties, active compositions in the form of mixtures of such compounds with solid and liquid dispersible carrier vehicles, and methods for producing such compounds and for using such compounds in a new way especially for combating pests, e.g. insects and acarids, with other and further objects becoming apparent from a study of the within specification and accompanying examples.

It is already known that certain phenoxybenzyl acetates or carboxylates, for example 3'-phenoxybenzyl α-isopropyl-(3,4-dimethoxy-phenyl)-acetate, 6-chloro-piperonyl 2,2-dimethyl-3-(2,2-dimethyl-vinyl)-cyclopropanecarboxylate and 3'-phenoxybenzyl 2,2-dimethyl-3-indenyl-cyclopropane-carboxylate, possess insecticidal and acaricidal properties (see German Offenlegungsschriften (German Published Specifications) 2,335,347 and 2,605,828 and U.S. Pat. No. 2,857,309).

The present invention now provides, as new compounds, the substituted phenoxybenzyloxycarbonyl derivatives of the general formula

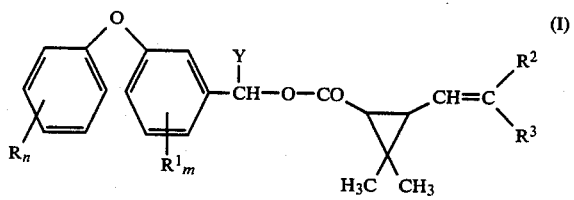

in which

R, R¹ and R², which need not be identical, each represent hydrogen or halogen,

R³ represents phenyl or phenylthio, and in either case the phenyl ring may optionally carry one or more substituents selected independently from alkyl groups and halogen atoms, Y represents hydrogen or nitrile, n represents 1, 2, 3, 4 or 5 and m represents 1, 2, 3 or 4.

These new compounds are distinguished by powerful insecticidal and acaricidal properties.

Preferably, R and R¹ each represent hydrogen or fluorine, R² represents hydrogen, chlorine or bromine, R³ represents phenyl, phenylthio, halogenophenyl (preferred halogens being chlorine or fluorine) or alkylphenyl, the alkyl radical of which has 1 to 6 (especially 1 to 4) carbon atoms and Y represents hydrogen or nitrile.

The general formula (I) here encompasses the various possible stereoisomers, the optical isomers and mixtures of these components.

The present invention also provides a process for the preparation of a substituted phenoxybenzyloxycarbonyl derivative (I), in which (a) a phenoxybenzyl alcohol of the general formula

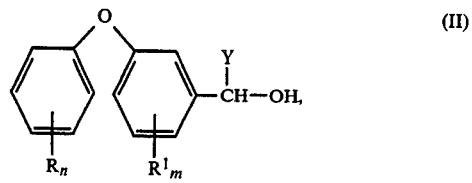

in which

R, R¹, Y, n and m have the above-mentioned meanings, is reacted with a cyclopropanecarboxylic acid derivative of the general formula

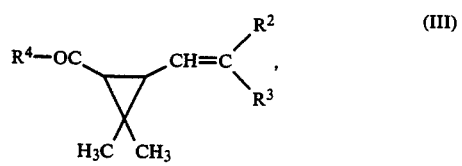

in which

R² and R³ have the above-mentioned meanings and

R⁴ represents halogen, preferably chlorine, or C₁₋₄-alkoxy, preferably methoxy or ethoxy, if appropriate in the presence of an acid acceptor and, if appropriate, in the presence of a diluent, or (b) a phenoxybenzyl halide of the general formula

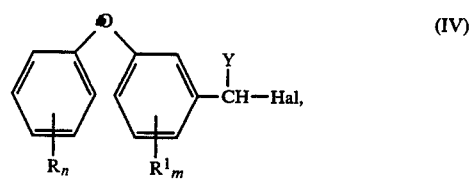

in which

R, R¹, Y, n and m have the above-mentioned meanings and

Hal represents halogen, preferably chlorine or bromine, is reacted, if appropriate in the presence of a diluent, with a cyclopropanecarboxylic acid derivative of the formula

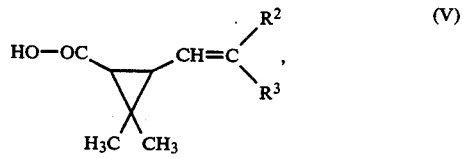

in which

R² and R³ have the above-mentioned meanings, the latter being employed either in the form of an alkali metal salt, alkaline earth metal salt or ammonium salt or as such in the presence of an acid acceptor.

Surprisingly, the substituted phenoxybenzyloxycarbonyl derivatives according to the invention exhibit a better insecticidal and acaricidal action than the corresponding previously known products of analogous structure and of the same type of action. The products according to the present invention thus represent a genuine enrichment of the art.

If, for example, 3-(4-fluorophenoxy)-benzyl alcohol and 2,2-dimethyl-3-(2-phenylvinyl)-cyclopropanecarboxylic acid chloride are used as starting materials in process variant (a) and the sodium salt of 2,2-dimethyl-3-(2-phenylthiovinyl)-cyclopropanecarboxylic acid and 3-phenoxy-α-cyano-benzyl bromide are used as starting materials in process variant (b), the courses of the reactions can be represented by the following equations:

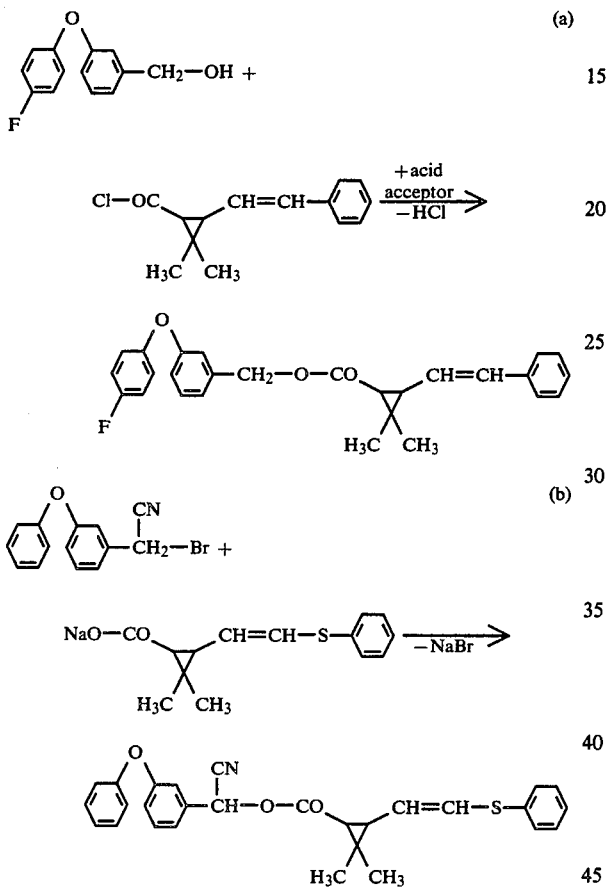

Phenoxybenzyl alcohols (II) to be used as starting compounds are known and can be prepared in accordance with generally customary processes described in the literature (see German Offenlegungsschrift (German Published Specification) 2,547,534).

The following are specific examples: 3-phenoxy-benzyl alcohol, 3-(4-fluorophenoxy)-benzyl alcohol, 3-(3-fluorophenoxy)-benzyl alcohol, 3-(2-fluorophenoxy)-benzyl alcohol, 3-phenoxy-4-fluoro-benzyl alcohol, 3-(4-fluorophenoxy)-4-fluoro-benzyl alcohol, 3-(3-fluorophenoxy)-4-fluoro-benzyl alcohol, 3-(2-fluorophenoxy)-4-fluoro-benzyl alcohol, 3-phenoxy-α-cyano-benzyl alcohol, 3-(4-fluorophenoxy)-α-cyano-benzyl alcohol, 3-(3-fluorophenoxy)-α-cyano-benzyl alcohol, 3-(2-fluorophenoxy)-α-cyanobenzyl alcohol, 3-phenoxy-4-fluoro-α-cyano-benzyl alcohol, 3-(4-fluorophenoxy)-4-fluoro-α-cyano-benzyl alcohol, 3-(3-fluorophenoxy)-4-fluoro-α-cyano-benzyl alcohol, 3-(2-(fluorophenoxy)-4-fluoro-α-cyano-benzyl alcohol, 3-phenoxy-6-fluoro-α-cyano-benzylalcohol, 3-(4-fluorophenoxy)-6-fluoro-α-cyano-benzyl alcohol, 3-(3-fluorophenoxy)-6-fluoro-α-cyano-benzyl alcohol and 3-(2-fluorophenoxy)-6-fluoro-α-cyano-benzyl alcohol.

The cyclopropanecarboxylic acid derivatives (V) also to be used as starting compounds can be prepared from the cyclopropane-carboxylic acid ethyl esters, known from Tetrahedron Letters 1976, 48, pages 4,359–4,362, by acid or alkaline saponification. The free acids are converted in accordance with known processes into the corresponding salts or acid halides (III) and (V). The ethyl esters, which are known, can in turn be prepared in accordance with processes known from the literature, for example from 2,2-dimethyl-3-formyl-cyclopropanecarboxylic acid ethyl ester and O,O-diethylmethanephosphonic acid diester derivatives in accordance with the following equation:

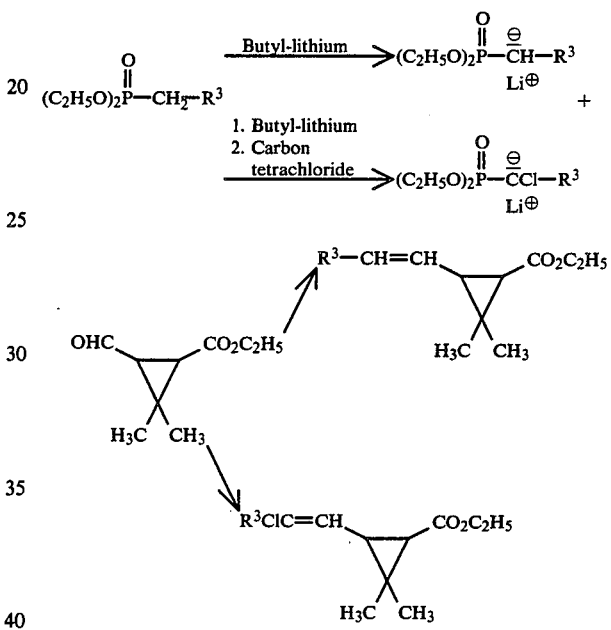

The following may be mentioned as specific examples of the cyclopropanecarboxylic acid derivatives (III) and (V): 3-[2-phenyl-vinyl]-, 3-[2-(2-chlorophenyl)-vinyl]-, 3-[2-(4-chlorophenyl)-vinyl]-, 3-[2-(3,4-dichlorophenyl)-vinyl]-, 3-[2-(4-fluorophenyl)-vinyl]-, 3-[2-pentachlorophenyl-vinyl]-, 3-[2-pentafluorophenyl-vinyl]-, 3-[2-phenylthio-vinyl]-, 3-[2-(2-chlorophenylthio)-vinyl]-, 3-[2-(4-chlorophenylthio)-vinyl]-, 3-[2-(3,4-dichlorophenylthio)-vinyl]-, 3[2-(4-fluorophenylthio)-vinyl]-, 3-[2-pentachlorophenylthio-vinyl]-, 3-[2-pentafluorophenylthio-vinyl]- and 3-[2-(4-tert.-butylphenyl)-vinyl]-2,2-dimethylcyclopropanecarboxylic acid and -2,2-dimethylcyclopropanecarboxylic acid chloride, as well as 3-[2-phenyl-2-chlorovinyl]-,3-[2-(2-chlorophenyl)-2-chloro-vinyl]-, 3-[2-(4chlorophenyl)-2-chloro-vinyl]-, 3-[2-(3,4-dichlorophenyl)-2-chlorovinyl]-, 3-[2-(4-fluorophenyl)-2-chloro-vinyl]-, 3-[2-pentachlorophenyl)-2-chloro-vinyl]-, 3-(2-pentafluorophenyl-2-chlorovinyl)-, 3-[2-phenylthio-2-chlorovinyl]-, 3-[2-(2-chlorophenylthio)-2-chloro-vinyl]-, 3-[2-(4-chlorophenylthio)-2-chlorovinyl]-, 3-[2-(3,4-dichlorophenylthio)-2-chloro-vinyl]-, 3-[2-(4-fluorophenylthio)-2-chloro-vinyl]-, 3-[2-pentachlorophenylthio-2-chloro-vinyl]-, 3-[2-pentafluorophenylthio-2-chloro-vinyl]- and 3-[2-(4-tert.-butylphenyl)-2-chloro-vinyl]-2,2-dimethylcyclopropanecarboxylic acid and -2,2-dimethylcyclopropanecarboxylic acid chloride, and also 3-[2-phenyl-2-bromovinyl]-, 3-[2-(2-chlorophenyl)-2-bromo-vinyl]-, 3-[2-(4-chlorophenyl)-2-bromovinyl]-, 3-[2-(3,4-dichlorophenyl)-2-bromo-vinyl]-, 3-[2-(4-fluorophenyl)-2-bromo-vinyl]-, 3-[2-pentachlorophenyl-2-bromovinyl]-, 3-(2-pentafluorophenyl-2-bromo-vinyl)-, 3-[2-phenylthio-2-bromo-vinyl]-, 3-[2-(2-chlorophenylthio)-2-bromo-vinyl]-, 3-[2-(4-chlorophenylthio)-2-bromo-vinyl]-, 3-[2-(3,4-dichlorophenylthio)-2-bromo-vinyl]-, 3-[2-(4-fluorophenylthio)-2-bromovinyl]-, 3-[2-pentachlorophenylthio-2-bromo-vinyl]-, 3-[2-pentafluorophenylthio-2-bromo-vinyl]- and 3-[2-(4-tert.-butylphenyl)-2-bromo-vinyl]-2,2-dimethylcyclopropanecarboxylic acid and -2,2-dimethylcyclopropanecarboxylic acid chloride.

In addition, the phenoxybenzyl halides (IV), which can also be prepared in accordance with processes known from the literature, are used as starting compounds. The following may be mentioned as specific examples of these: 3-phenoxybenzyl chloride and -benzyl bromide, 3-(4-fluorophenoxy)benzyl chloride and -benzyl bromide, 3-(3-fluorophenoxy)benzyl chloride and -benzyl bromide, 3-(2-fluorophenoxy)benzyl chloride and -benzyl bromide, 3-phenoxy-4-fluorobenzyl chloride and -benzyl bromide, 3-(4-fluorophenoxy)-4-fluoro-benzyl chloride and -benzyl bromide, 3-(3-fluorophenoxy)-4-fluoro-benzyl chloride and -benzyl bromide, 3-(2-fluorophenoxy)-4-fluoro-benzyl chloride and -benzyl bromide, 3-phenoxy-α-cyano-benzyl chloride and -benzyl bromide, 3-(4-fluorophenoxy)-α-cyano-benzyl chloride and -benzyl bromide, 3-(3-fluorophenoxy)-α-cyano-benzyl chloride and -benzyl bromide, 3-(2-fluorophenoxy)-α-cyano-benzyl chloride and -benzyl bromide, 3-phenoxy-4-fluoro-α-cyano-benzyl chloride and -benzyl bromide, 3-(4-fluorophenoxy)-4-fluoro-α-cyano-benzyl chloride and -benzyl bromide, 3-(3-fluorophenoxy)-4-fluoro-α-cyano-benzyl chloride and -benzyl bromide, 3-(2-fluorophenoxy)-4-fluoro-α-cyano-benzyl chloride and -benzyl bromide, 3-phenoxy-6-fluoro-α-cyano-benzyl chloride and -benzyl bromide, 3-(4-fluoro-phenoxy)-6-fluoro-α-cyano-benzyl chloride and -benzyl bromide, 3-(3-fluorophenoxy)-6-fluoro-α-cyano-benzyl chloride and -benzyl bromide and 3-(2-fluorophenoxy)-6-fluoro-α-cyano-benzyl chloride and -benzyl bromide.

All customary acid-binding agents can be used as acid acceptors. Alkali metal carbonates and alkali metal alcoholates, such as sodium carbonate, potassium carbonate, sodium methylate, sodium ethylate, potassium methylate and potassium ethylate have proved particularly suitable, as have aliphatic, aromatic or heterocyclic amines, for example triethylamine, trimethylamine, dimethylaniline, dimethylbenzylamine and pyridine.

The reaction temperature can be varied within a substantial range. In general, the reaction is carried out at between 0° and 150° C., preferably at from 10° to 40° C. in process variant (a) and at from 100° to 130° C. in process variant (b).

The reaction is in general allowed to take place under normal pressure.

Process variants (a) and (b) for the preparation of the compounds according to the invention are preferably carried out in the presence of a suitable diluent. Virtually all inert organic solvents can be used for this purpose, especially aliphatic and aromatic, optionally chlorinated, hydrocarbons, such as benzene, toluene, xylene, benzine, methylene chloride, chloroform, carbon tetrachloride and chlorobenzene; ethers, for example diethyl ether, dibutyl ether and dioxane; ketones, for example acetone, methyl ethyl ketone, methyl isopropyl ketone and methyl isobutyl ketone; nitriles, such as acetonitrile and propionitrile; and formamides, for example dimethylformamide.

To carry out process variant (a), the starting materials are preferably employed in equimolar amounts. An excess of one or other reactant produces no significant advantages. In most cases, the reactants are brought together in one of the stated solvents and are stirred in the presence of an acid acceptor, in most cases at an elevated temperature, for one or more hours. The reaction mixture is then worked up by pouring it into water, separating off the organic phase and then working up the latter in the usual manner by washing, drying and distilling off the solvent.

In the case of the transesterification according to process variant (a), the procedure followed in the usual manner is to take the methyl ester or ethyl ester of the cyclopropanecarboxylic acid, if appropriate in a suitable solvent, together with 10–30% excess of the alcohol of the formula (II), and heat the mixture with addition of alkali metal methylate or alkali metal ethylate. The lower-boiling alcohol produced is at the same time distilled off continuously.

In carrying out process variant (b), the cyclopropanecarboxylic acid derivative is preferably employed in the form of an alkali metal salt. This salt, in one of the stated solvents, is heated with the benzyl halide derivative to 80°–140° C. An excess of one or the other reactant produces no advantages. After completion of the reaction, the solvent is distilled off, the residue is taken up in methylene chloride and the organic phase is worked up as described above.

The new compounds are obtained in the form of oils, which in most cases cannot be distilled without decomposition but are freed from the last volatile constituents by so-called "incipient distillation", that is to say by prolonged heating under reduced pressure to moderately elevated temperatures, and are purified in this manner. They are characterized by the refractive index or the boiling point.

The substituted phenoxybenzyloxycarbonyl derivatives according to the invention are not only active against plant pests, pests harmful to health and pests of stored products, but also, in the veterinary medicine field, against animal parasites (ectoparasites), such as parasitic fly larvae and ticks.

The active compounds are well tolerated by plants, have a favorable level of toxicity to warm-blooded animals, and can be used for combating arthropod pests, especially insects and acarids, which are encountered in agriculture, in forestry, in the protection of stored products and of materials, and in the hygiene field. They are active against normally sensitive and resistant species and against all or some stages of development. The abovementioned pests include:

from the class of the Isopoda, for example *Oniscus asellus, Armadillidium vulgare* and *Porcellio scaber;* from the class of Diplopoda, for example *Blaniulus guttulatus;* from the class of the Chilopoda, for example *Geophilus carpophagus* and Scutigera spec.;

from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria;* from the order of the Dermaptera, for example *Forficula auricularia;* from the order of the Isoptera, for example Reticulitermes spp.;

from the order of the Anoplura, for example *Phylloxera vastatrix,* Pemphigus spp., *Pediculus humanus corporis,* Haematopinus spp. and Lingnathus spp.;

from the order of the Mallophaga, for example Trichodectes spp. and Damalinea spp.;

from the order of the Thysanoptera, for example *Hercinothrips femoralis* and *Thrips tabaci;* from the order of the Heteroptera, for example Eurygaster spp., *Dysdercus intermedius, Piesma quadrata, Cimex lectularius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiells aurantii, Aspidiotus hederae,* Pseudococcus spp. and Psylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citerella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Cacoecia podana, Capua reticulane, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psyllodies,* Tribolium spp., *Tenebric molitor,* Agriotes spp., Conoderus spp., *Melolontha melolontha, Amphimallon solstitialis* and *Costelytra zealandica;* from the order of the Hymenoptera, for example Diprion spp., Hoplocampa spp., Lasius spp., *Monomorium pharanois* and Vespa spp.;

from the order of the Diptera, for example Aedes spp., Anopheles spp., Culex spp., *Drosophila melanogaster,* Musca spp., Fannia spp., Calliphora erythroecphala, Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp.;

from the class of the Arachnida, for example *Scorpio maurus* and *Latrodectus mactans;* from the order of the Acarina, for example Acarus siro, Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

The active compounds can be converted into the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid solvents diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention may be used in the form of their formulations of the types that are commercially available or in the use forms prepared from these formulations.

The active compound content of the use forms prepared from the formulations of the types that are commercially available can vary within wide ranges. The active compound concentration of the use forms can be from 0.0000001 to 100% by weight of active compound, preferably from 0.01 to 10% by weight.

The compounds may be employed in a customary manner appropriate for the particular use forms.

When used against pests harmful to health and pests of stored products, the active compounds are distinguished by an excellent residual activity on wood and clay as well as a good stability to alkali on limed substrates.

In the veterinary field, the active compounds according to the invention may be used in a known manner, such as orally in the form of, for example, tablets, capsules, drenches and granules; dermally by means of, for example, dipping, spraying, pouring-on, spotting-on and powdering; and parenterally, for example by means of injections.

The present invention also provides an arthropodicidal composition containing as active ingredient a compound of the present invention in admixture with a solid or liquefied gaseous diluent or carrier or in admixture with a liquid diluent or carrier containing a surface-active agent.

The present invention also provides a method of combating arthropods (especially insects or acarids) which comprises applying to the arthropods, or to a habitat thereof, a compound of the present invention alone or in the form of a composition containing as active ingredient a compound of the present inmention in admixture with a diluent or carrier.

The present invention also provides a method of freeing or protecting domesticated animals from ectoparasitical insects or acarids which comprises applying to said animals a compound according to the present invention, in admixture with a diluent or carrier.

The present invention further provides crops protected from damage by arthropods by being grown in areas in which immediately prior to and/or during the time of the growing a compound of the present invention was applied alone or in admixture with a diluent or carrier.

It will be seen that the usual methods for providing a harvested crop may be improved by the present invention.

The present invention further provides domesticated animals whenever freed or protected from ectoparasitical insects or acarids by the application to said animals of a compound according to the present invention, in admixture with a diluent or carrier.

The cyclopropanecarboxylic acids (V), or their salts and acid chlorides (III) required as starting compounds, could be prepared as follows:

EXAMPLE 1

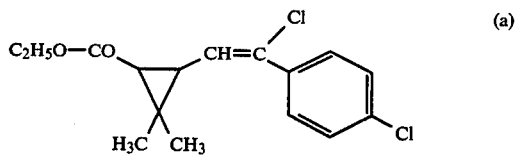

(a)

26.3 g (0.1 mol) or 4-chlorobenzyl-phosphonic acid diethyl ester were dissolved in 400 ml of absolute tetrahydrofuran and the solution was cooled to $-70°$ C. 0.11 mol of n-butyl-lithium (as a 15% strength solution in hexane) were added dropwise under a counter-current of nitrogen and while stirring well, and the reaction mixture was then stirred for a further 15 minutes at $-70°$ C. Thereafter, 15.4 g (0.1 mol) of carbon tetrachloride were added dropwise at $-70°$ C., still under nitrogen; in the course thereof, the reaction mixture assumed a red-brown color. After stirring for a further 15 minutes, 18.6 g (0.1 mol) of 2,2-dimethyl-3-formyl-cyclopropanecarboxylic acid ethyl ester were added at $-65°$ C. The reaction mixture was then allowed to come to room temperature and was stirred for a further 3 hours at 25° C. The reaction batch was then poured into 2 liters of water and extracted with 600 ml of ether. The ether phase was dried over sodium sulphate, the solvent was stripped off in vacuum and the oily residue was distilled at 150°–155° C./2 mm Hg. 2,2-Dimethyl-3-(2-chloro-2-p-chlorophenyl-vinyl)-cyclopropanecarboxylic acid ethyl ether was obtained in 54.3% yield.

The following could be prepared analogously:

TABLE 1

| Formula | Yield (% of theory) | Physical data (refractive index; boiling point, °C./mm Hg) |
|---|---|---|
| C₂H₅O—CO—[cyclopropane(CH₃)₂]—CH=C(Cl)(C₆H₅) | 48 | $n_D^{23}$: 1.5222 |

TABLE 1-continued

| Formula | Yield (% of theory) | Physical data (refractive index; boiling point, °C./mm Hg) |
|---|---|---|
| C₂H₅O—CO—[cyclopropane(H₃C,CH₃)]—CH=C(Cl)—(3,4-dichlorophenyl) | 45.4 | $n_D^{25}$: 1.5621 |
| C₂H₅O—CO—[cyclopropane(H₃C,CH₃)]—CH=C(Cl)—(2-chlorophenyl) | 52.7 | 155–160/1 |
| C₂H₅O—CO—[cyclopropane(H₃C,CH₃)]—CH=C(Cl)—(4-fluorophenyl) | 57 | $n_D^{25}$: 1.5208 |
| C₂H₅O—CO—[cyclopropane(H₃C,CH₃)]—CH=C(Cl)—S—(4-chlorophenyl) | 81 | $n_D^{25}$: 1.5025 |
| C₂H₅O—CO—[cyclopropane(H₃C,CH₃)]—CH=C(Cl)—S—phenyl | 71 | $n_D^{26}$: 1.5359 |

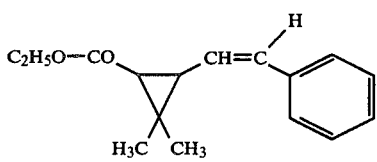

(b)

22.8 g (0.1 mol) of benzylphosphonic acid diethyl ester were dissolved in 400 ml of absolute tetrahydrofuran and the solution was cooled to −70° C. 0.11 mol of n-butyl-lithium (as a 15% strength solution in hexane) were added dropwise under a counter-current of nitrogen and while stirring well; the mixture was then stirred at −70° C. for a further 15 minutes, and thereafter 18.6 g (0.1 mol) of 2,2-dimethyl-3-formyl-cyclopropanecarboxylic acid ethyl ester were added dropwise at −65° C., again still under nitrogen. The reaction mixture was then allowed to come to room temperature and was stirred further for 3 hours at 25° C. Thereafter, the reaction batch was poured into 2 liters of water and extracted with 600 ml of ether. The ether phase was dried over sodium sulphate and the solvent was then stripped off in vacuo. The oily residue was distilled at 145°–150° C./3 mm Hg. 2,2-Dimethyl-3-(2-phenyl-vinyl)-cyclopropanecarboxylic acid ethyl ester having a refractive index $n_D^{23}$ of 1.5022 was obtained in 69.6% yield.

The following could be prepared analogously:

TABLE 2

| Formula | Yield (% theory) | Physical data (refractive index; boiling point, °C./mm Hg) |
|---|---|---|
| C₂H₅O—CO—[cyclopropane(H₃C,CH₃)]—CH=C(H)—(3,4-dichlorophenyl) | 70.2 | $n_D^{25}$: 1.5584 |

TABLE 2-continued

| Formula | Yield (% theory) | Physical data (refractive index; boiling point, °C./mm Hg) |
|---|---|---|
| C₂H₅O—CO—[cyclopropane(H₃C,CH₃)]—CH=C(H)(4-F-C₆H₄) | 49.6 | $n_D^{25}$: 1.5057 |
| C₂H₅O—CO—[cyclopropane(H₃C,CH₃)]—CH=C(H)(2-Cl-C₆H₄) | 46 | 150–155/1 |

The cyclopropanecarboxylic acid ethyl esters prepared according to (a) or (b) were subjected to acid or alkaline saponification, in accordance with known methods, to give the corresponding acids. These were converted, in accordance with methods which are also known, into the corresponding salts (for example alkali metal salts or ammonium salts) or acid chlorides. These in turn were converted to the novel esters as follows:

EXAMPLE 2

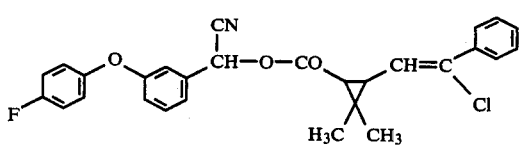

(1)

7.3 g (0.03 mol) of 3-(4-fluorophenoxy)-α-cyanobenzyl alcohol and 8.1 g (0.03 mol) of 2,2-dimethyl-3-(2-phenyl-2-chlorovinyl)-cyclopropanecarboxylic acid chloride were dissolved in 150 ml of anhydrous toluene and 2.4 g (0.03 mol) of pyridine, dissolved in 50 ml of toluene, were added dropwise at 25°–30° C., while stirring. Thereafter, stirring was continued for 3 hours at 25° C. The reaction mixture was poured into 150 ml of water and the organic phase was separated off and again washed, with 100 ml of water. The toluene phase was then dried over sodium sulphate and the solvent was distilled off under a water-pump vacuum. The last remnants of solvent were removed by brief incipient distillation under 1 mm Hg at 60° C. bath temperature. 12.0 g (84% of theory) of 3'-(4-fluorophenoxy)-α-cyanobenzyl 2,2-dimethyl-3-(2-phenyl-2-chlorovinyl)-cyclopropane carboxylate were obtained as a yellow oil having a refractive index $n_D^{24}$ of 1.5670.

EXAMPLE 3

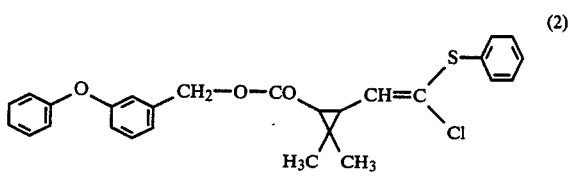

(2)

24.3 g (0.05 mol) of the sodium salt of 2,2-dimethyl-3-(2-phenylthio-2-chlorovinyl)-cyclopropanecarboxylic acid were dissolved in 150 ml of dimethylformamide and heated to 120° C., together with 15.8 g (0.06 mol) of 3-phenoxybenzyl bromide for 4 hours. After completion of the reaction, the dimethylformamide was distilled off in vacuo and the residue was taken up in 200 ml of methylene chloride. It was then extracted by shaking with twice 150 ml of water, the organic phase was dried over sodium sulphate and the solvent was stripped off in vacuo. The last remnants of solvent were removed by brief incipient distillation under 1 mm Hg at 60° C. bath temperature. 15 g (53.8% of theory) of 3'-phenoxy-benzyl 2,2-dimethyl-3-(2-phenylthio-2-chlorovinyl)-cyclopropane carboxylic were obtained as a yellow oil having a refractive index $n_D^{23}$ of 1.5948.

The following compounds could be prepared analogously:

TABLE 3

| Compound No. | Formula | Yield (% of theory) | Refractive index: |
|---|---|---|---|
| 3 | 4-F-C₆H₄-O-C₆H₄-CH₂-O-CO-[cyclopropane(H₃C,CH₃)]-CH=C(H)(3,4-Cl₂-C₆H₃) | 72 | $n_D^{22}$:1.5851 |
| 4 | C₆H₅-O-C₆H₄-CH₂-O-CO-[cyclopropane(H₃C,CH₃)]-CH=C(Cl)(3,4-Cl₂-C₆H₃) | 49.8 | $n_D^{24}$:1.5872 |

TABLE 3-continued
| Compound No. | Formula | Yield (% of theory) | Refractive index: |
|---|---|---|---|
| 5 | 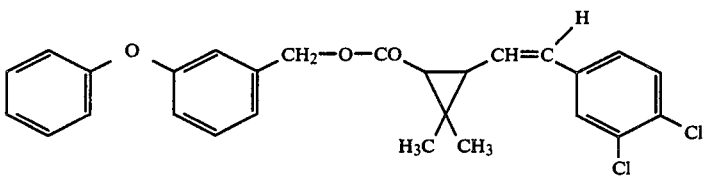 | 73.9 | $n_D^{24}$:1.6014 |
| 6 | 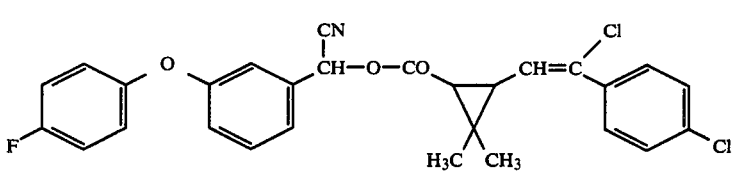 | 71 | $n_D^{24}$:1.5705 |
| 7 | 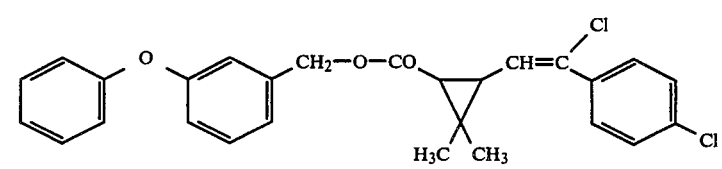 | 58.9 | $n_D^{23}$:1.5914 |
| 8 | 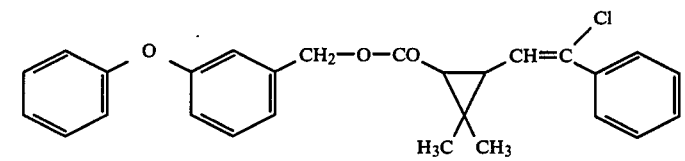 | 67.5 | $n_D^{23}$:1.5782 |
| 9 | 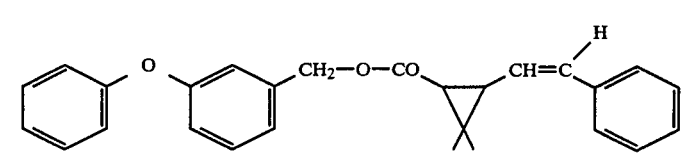 | 82 | $n_D^{23}$:1.5805 |
| 10 | 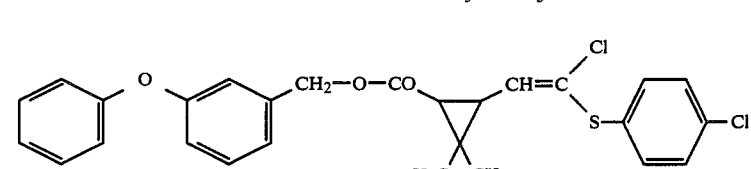 | 47 | $n_D^{24}$:1.6017 |
| 11 | 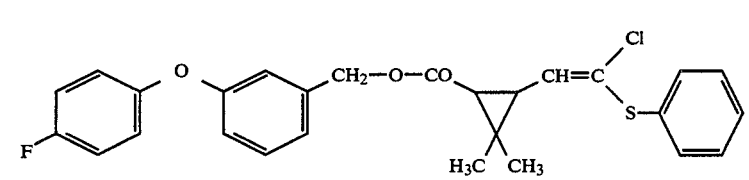 | 51.9 | $n_D^{23}$:1.5961 |
| 12 | 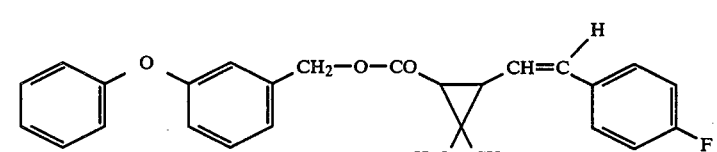 | 62.5 | $n_D^{26}$:1.5762 |
| 13 | 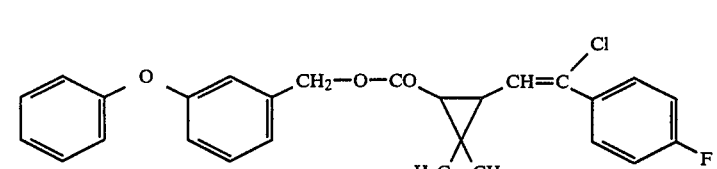 | 66.6 | $n_D^{26}$:1.5790 |

TABLE 3-continued

| Compound No. | Formula | Yield (% of theory) | Refractive index: |
|---|---|---|---|
| 14 | (3-phenoxyphenyl)(CN)CH–O–CO–cyclopropane(2,2-diMe)–CH=C(Cl)(4-F-phenyl) | | |
| 15 | (3-phenoxyphenyl)(CN)CH–O–CO–cyclopropane(2,2-diMe)–CH=CH(4-Cl-phenyl) | 73.4 | $n_D^{25}$:1.5879 |
| 16 | (3-phenoxyphenyl)(CN)CH–O–CO–cyclopropane(2,2-diMe)–CH=C(Cl)(4-Cl-phenyl) | 82.2 | $n_D^{25}$:1.5900 |
| 17 | (3-phenoxy-4-F-phenyl)(CN)CH–O–CO–cyclopropane(2,2-diMe)–CH=C(Cl)(4-Cl-phenyl) | 85.2 | $n_D^{25}$:1.5831 |
| 18 | (3-phenoxyphenyl)CH$_2$–O–CO–cyclopropane(2,2-diMe)–CH=CH(2-Cl-phenyl) | 74.0 | $n_D^{25}$:1.5945 |
| 19 | (3-phenoxyphenyl)CH$_2$–O–CO–cyclopropane(2,2-diMe)–CH=C(Cl)(2-Cl-phenyl) | 68.3 | $n_D^{25}$:1.5896 |
| 20 | (3-phenoxyphenyl)(CN)CH–O–CO–cyclopropane(2,2-diMe)–CH=C(Cl)(2-Cl-phenyl) | | |
| 21 | (3-phenoxy-4-F-phenyl)(CN)CH–O–CO–cyclopropane(2,2-diMe)–CH=C(Cl)(2-Cl-phenyl) | | |
| 22 | (3-phenoxyphenyl)CH$_2$–O–CO–cyclopropane(2,2-diMe)–CH=C(Br)(phenyl) | | |

TABLE 3-continued

| Compound No. | Formula | Yield (% of theory) | Refractive index: |
|---|---|---|---|
| 23 | (phenyl)-O-(phenyl)-CH(CN)-O-CO-(cyclopropyl with H₃C, CH₃)-CH=C(Br)-(phenyl)-Cl | | |
| 24 | (phenyl)-O-(phenyl)-CH(CN)-O-CO-(cyclopropyl with H₃C, CH₃)-CH=C(H)-(C₆F₅) | | |
| 25 | (phenyl)-O-(phenyl)-CH(CN)-O-CO-(cyclopropyl with H₃C, CH₃)-CH=C(Cl)-(C₆F₅) | | |
| 26 | (phenyl)-O-(phenyl)-CH₂-O-CO-(cyclopropyl with H₃C, CH₃)-CH=C(Cl)-(phenyl)-C(CH₃)₃ | | |
| 27 | (phenyl)-O-(phenyl)-CH(CN)-O-CO-(cyclopropyl with H₃C, CH₃)-CH=C(Cl)-S-(phenyl)-Cl | 80.4 | $n_D^{30}$:1.5990 |
| 28 | (phenyl)-O-(phenyl)-CH(CN)-O-CO-(cyclopropyl with H₃C, CH₃)-CH=C(Cl)-S-(phenyl) | | |
| 29 | (phenyl)-O-(phenyl with F)-CH(CN)-O-CO-(cyclopropyl with H₃C, CH₃)-CH=C(H)-S-(phenyl)-Cl | | |
| 30 | (phenyl)-O-(phenyl)-CH(CN)-O-CO-(cyclopropyl with H₃C, CH₃)-CH=C(H)-S-(C₆Cl₅) | | |
| 31 | (phenyl)-O-(phenyl)-CH₂-O-CO-(cyclopropyl with H₃C, CH₃)-CH=C(Cl)-S-(C₆Cl₅) | | |

TABLE 3-continued

| Compound No. | Formula | Yield (% of theory) | Refractive index: |
|---|---|---|---|
| 32 | | | |
| 33 | | 88.7 | $n_D^{25}$:1.5868 |
| 34 | | 54.3 | |
| 35 | | 57.8 | $n_D^{30}$:1.5978 |
| 36 | | 76.7 | |
| 37 | | 39.8 | |
| 38 | | 77.0 | $n_D^{24}$:1.5829 |

The insecticidal and acaricidal activity of the compounds of this invention is illustrated by the following examples wherein the compounds according to the present invention are each identified by the number (given in brackets) from preparative Examples 2 and 3.

The known comparison compounds are identified as follows:

(A) = 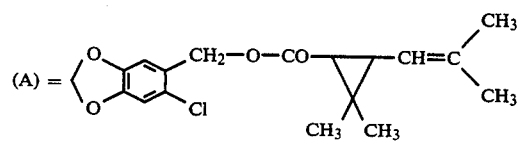

-continued

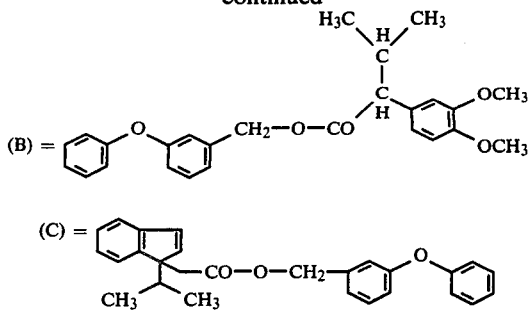

EXAMPLE 4

Phaedon larvae test
Solvent: 3 parts by weight of dimethylformamide
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage leaves (*Brassica oleracea*) were sprayed with the preparation of the active compound until dripping wet and were then infested with mustard beetle larvae (*Phaedon cochleariae*).

After the specified periods of time, the degree of destruction was determined in %: 100% meant that all of the beetle larvae had been killed whereas 0% meant that none of the beetle larvae had been killed.

The active compounds, the concentrations of the active compounds, the evaluation times and the results can be seen from the following table:

TABLE 4

| | (insects which damage plants) Phaedon larvae test | |
|---|---|---|
| Active compounds | Active compound concentration in % | Degree of destruction in % after 3 days |
| (A) | 0.1 | 100 |
| | 0.01 | 100 |
| | 0.001 | 0 |
| (B) | 0.1 | 100 |
| | 0.01 | 90 |
| | 0.001 | 0 |
| (2) | 0.1 | 100 |
| | 0.01 | 100 |
| | 0.001 | 100 |
| (10) | 0.1 | 100 |
| | 0.01 | 100 |
| | 0.001 | 100 |
| (1) | 0.1 | 100 |
| | 0.01 | 100 |
| | 0.001 | 100 |

EXAMPLE 5

Myzus test (contact action)
Solvent: 3 parts by weight of dimethylformamide
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage plants (*Brassica oleracea*) which had been heavily infested with peach aphids (*Myzus persicae*) were sprayed with the preparation of the active compound until dripping wet.

After the specified periods of time, the degree of destruction was determined as a percentage: 100% meant that all of the aphids were killed whereas 0% meant that none of the aphids were killed.

The active compounds, the concentrations of the active compounds, the evaluation times and the results can be seen from the following table:

TABLE 5

| | (insects which damage plants) Myzus test | |
|---|---|---|
| Active compounds | Active compound concentration in % | Degree of destruction in % after 1 day |
| (C) | 0.1 | 50 |
| | 0.01 | 0 |
| (2) | 0.1 | 100 |
| | 0.01 | 100 |
| (7) | 0.1 | 100 |
| | 0.01 | 90 |
| (10) | 0.1 | 100 |
| | 0.01 | 90 |
| (11) | 0.1 | 100 |
| | 0.01 | 95 |
| (1) | 0.1 | 100 |
| | 0.01 | 100 |
| (6) | 0.1 | 100 |
| | 0.01 | 100 |

EXAMPLE 6

Tetranychus test (resistant)
Solvent: 3 parts by weight of dimethylformamide
Emulsifier: 1 part by weight of alkylaryl polyglycol ether To produce a suitable preparation of active compound, 1 part by weight of the active compound was mixed with the stated amount of solvent and the stated amount of emulsifier and the concentrate was diluted with water to the desired concentration.

Bean plants (*Phaseolus vulgaris*) which were heavily infested with the two-spotted spider mite (*Tetranychus urticae*) in all stages of development were sprayed with the preparation of the active compound until dripping wet.

After the specified periods of time, the degree of destruction was determined as a percentage: 100% meant that all of the spider mites were killed whereas 0% meant that none of the spider mites were killed.

The active compounds, the concentrations of the active compounds, the evaluation times and the results can be seen from the following table:

TABLE 6

| | (Mites which damage plants) Tetranychus test | |
|---|---|---|
| Active compound | Active compound concentration in % | Degree of destruction in % after 2 days |
| (A) | 0.1 | 0 |
| (C) | 0.1 | 0 |
| (2) | 0.1 | 90 |
| (7) | 0.1 | 98 |
| (4) | 0.1 | 98 |
| (11) | 0.1 | 90 |
| (1) | 0.1 | 98 |
| (6) | 0.1 | 100 |

EXAMPLE 7

Test with parasitic adult cattle ticks
Solvent: alkylaryl polyglycol ether

To produce a suitable preparation of an active compound, that compound was mixed with the stated solvent in the ratio of 1:2 and the concentrate thus obtained was diluted with water to the desired concentration.

10 adult cattle ticks (*Boophilus microplus* res.) were dipped for 1 minute in the preparation of active compound to be tested. After transferring the ticks into a plastic beaker and keeping them in a climatically controlled chamber, the degree of destruction in percent was determined, with 100% denoting that all of the ticks had been killed and 0% denoting that no ticks had been killed.

The results are shown in the following table.

TABLE 7

| Active compound | Active compound concentration in ppm | Degree of destruction in % |
| --- | --- | --- |
| (7) | 10,000 | 100 |

EXAMPLE 8

Test with parasitic fly larvae
Emulsifier: 80 parts by weight of alkylaryl glycol ether To produce a suitable preparation of active compound, 20 parts by weight of the active compound in question were mixed with the stated amount of the emulsifier and the mixture thus obtained was diluted with water to the desired concentration.

About 20 fly larvae (*Lucilia cuprina*) were introduced into a test tube which contained about 3 ml of a 20% strength suspension of egg yolk powder in water, and which was fitted with a cottonwool plug of appropriate size. 0.5 ml of the active compound preparation was placed on this egg yolk powder suspension. After 24 hours, the degree of destruction in % was determined. 100% meant that all of the larvae had been killed and 0% meant that none of the larvae had been killed.

The active compound, amounts used and results can be seen from the table which follows:

TABLE 8

| Active compound | Active compound concentration in ppm | Destructive action in % |
| --- | --- | --- |
| (2) | 1,000 | 100 |
| (10) | 1,000 | 100 |

It will be appreciated that the instant specification and examples are set forth by way of illustration and not limitation, and that various modifications and changes may be made without departing from the spirit and scope of the present invention.

What is claimed is:

1. A 3-phenoxybenzyl 2,2-dimethyl-3-vinyl-cyclopropane carboxylate of the formula

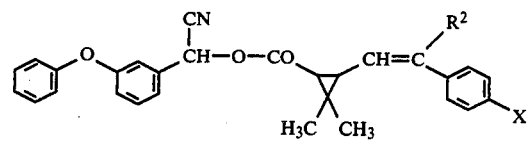

in which
R² is chlorine or bromine, and
X is Cl or F.

2. A carboxylate according to claim 1 wherein such carboxylate is 3'-phenoxy-α-cyanobenzyl 2,2-dimethyl-3-(2-(4-fluorophenyl)-2-chlorovinyl)-cyclopropane carboxylate of the formula

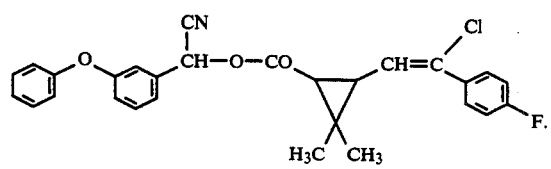

3. A carboxylate according to claim 1 wherein such carboxylate is 3'-phenoxy-α-cyanobenzyl 2,2-dimethyl-3-(2-(4-chlorophenyl)-2-chlorovinyl)-cyclopropane carboxylate of the formula

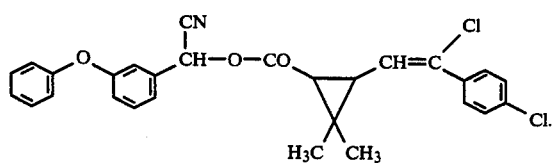

4. A carboxylate according to claim 1 wherein such carboxylate is 3'-phenoxy-α-cyanobenzyl 2,2-dimethyl-3-(2-(4-chlorophenyl)-2-bromovinyl)-cyclopropane carboxylate of the formula

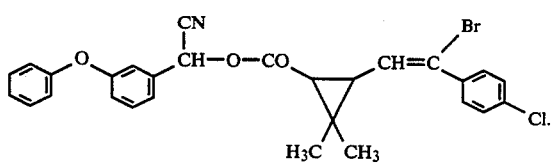

5. An arthropodicidal composition containing as active ingredient an arthropodicidally effective amount of a carboxylate according to claim 1 in admixture with a diluent.

6. A method of combating arthropods which comprises applying to the arthropods, or to a habitat thereof, an arthropodicidally effective amount of a carboxylate according to claim 1.

7. The method according to claim 6, wherein such compound is
3'-phenoxy-α-cyanobenzyl 2,2-dimethyl-3-(2-(4-fluorophenyl)-2-chlorovinyl)-cyclopropane carboxylate,
3'-phenoxy-α-cyanobenzyl 2,2-dimethyl-3-(2-(4-chlorophenyl)-2-chlorovinyl)-cyclopropane carboxylate or
3'-phenoxy-α-cyanobenzyl 2,2-dimethyl-3-(2-(4-chlorophenyl)-2-bromovinyl)-cyclopropane carboxylate.

* * * * *